United States Patent
Ume et al.

(10) Patent No.: US 7,762,136 B2
(45) Date of Patent: Jul. 27, 2010

(54) ULTRASOUND SYSTEMS AND METHOD FOR MEASURING WELD PENETRATION DEPTH IN REAL TIME AND OFF LINE

(75) Inventors: Ifeanyi C. Ume, Atlanta, GA (US); Akio Kita, Katy, TX (US)

(73) Assignee: Georgia Tech Research Corporation, Atlanta, GA (US)

( * ) Notice: Subject to any disclaimer, the term of this patent is extended or adjusted under 35 U.S.C. 154(b) by 301 days.

(21) Appl. No.: 11/895,217

(22) Filed: Aug. 23, 2007

(65) Prior Publication Data
US 2008/0072674 A1   Mar. 27, 2008

Related U.S. Application Data

(63) Continuation of application No. PCT/US2005/040495, filed on Nov. 7, 2005.

(51) Int. Cl.
*G01N 29/07* (2006.01)
(52) U.S. Cl. .............. 73/597; 73/598; 73/602; 73/622
(58) Field of Classification Search ........... 73/597, 73/598, 600, 602, 618, 624, 625, 627, 628
See application file for complete search history.

(56) References Cited

U.S. PATENT DOCUMENTS

| | | | |
|---|---|---|---|
| 4,406,167 A | | 9/1983 | Maeda |
| 4,570,387 A | * | 2/1986 | Unno et al. ............... 451/5 |
| 4,588,873 A | | 5/1986 | Fenn et al. |
| 4,693,120 A | * | 9/1987 | Robinson ............... 73/618 |
| 5,583,292 A | | 12/1996 | Karbach et al. |
| 5,726,349 A | * | 3/1998 | Palmertree et al. ............ 73/84 |
| 5,767,408 A | * | 6/1998 | Lindgren et al. ............ 73/597 |
| 5,894,092 A | * | 4/1999 | Lindgren et al. ............ 73/598 |
| 6,125,705 A | | 10/2000 | Johnson |
| 6,188,041 B1 | | 2/2001 | Kim et al. |
| 6,818,854 B2 | | 11/2004 | Friedman et al. |
| 7,415,880 B2 | * | 8/2008 | Renzel ............... 73/597 |

* cited by examiner

FOREIGN PATENT DOCUMENTS

WO   2006068716 A1   6/2006

OTHER PUBLICATIONS

International Preliminary Report on Patentability, Written Opinion of International Searching Authority, and International Search Report for PCT Patent Application No. PCT/US2005/40495, Issued by USPTO on Apr. 4, 2006 and Issued by WIPO on Jun. 26, 2007.

*Primary Examiner*—J M Saint Surin
(74) *Attorney, Agent, or Firm*—Troutman Sanders LLP; Ryan A Schneider; James H Yancey, Jr.

(57) ABSTRACT

Disclosed are systems and methods that permit both real-time, and off-line, measurement of weld penetration depth. Exemplary systems and methods comprise an ultrasound source, such as a pulsed Nd:Yag laser, that simultaneously generates longitudinal and shear waves that radiate adjacent one side of a weld joining two specimens. An ultrasonic sensor, such as an electro-magnetic acoustic transducer or a piezo-electric transducer, capable of detecting shear and/or longitudinal waves, is disposed on an opposite side of the weld from the source. A signal processor is coupled to the sensor that processes time of flight signals for selected longitudinal or shear waves transmitted across the weld seam. The signal processor implements an algorithm that computes the weld penetration depth from the time of flight signals.

13 Claims, 4 Drawing Sheets

Fig. 4

ULTRASOUND SYSTEMS AND METHOD FOR MEASURING WELD PENETRATION DEPTH IN REAL TIME AND OFF LINE

PRIORITY CLAIM & CROSS-REFERENCE TO RELATED APPLICATION

This application is a continuation of International Application No. PCT/US05/40495, filed 7 Nov. 2005.

BACKGROUND

The present invention relates generally to ultrasound systems and methods that provide for both real-time, and off-line, measurement of weld penetration depth.

Gas metal arc welding is one of the most common techniques used to join components together. Welds are conventionally tested after the welding process. As a result, a malformed or weak weld must be cut out and the components welded again or the component must be scrapped. Full closed loop control and automation of the welding process is being actively pursued to improve quality, reduce waste, and increase efficiency.

A major obstacle to fully automated welding is a lack of accurate, high resolution, non-destructive, and non-contact techniques to measure weld penetration depth that may be used in high temperatures and harsh environments typical of welding processes. There have been attempts to use machine vision, thermal distribution sensors, and though-the-arc sensing of current to indirectly measure weld penetration depth. However, all of these methods have had very limited success.

It would be desirable to have improved ultrasound systems and methods that allow real-time, and off-line, measurement of weld penetration depth.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Disclosed herein are ultrasound weld penetration depth measurement systems 10 that use ultrasound generation and reception methods 40 to directly measure weld penetration depth accurately and precisely. Reduced-to-practice systems 10 have produced repeatable results and can be used on-line during welding as well as off-line after welding. Real-time control of the welding process is made possible using this systems 10.

Figure 1:
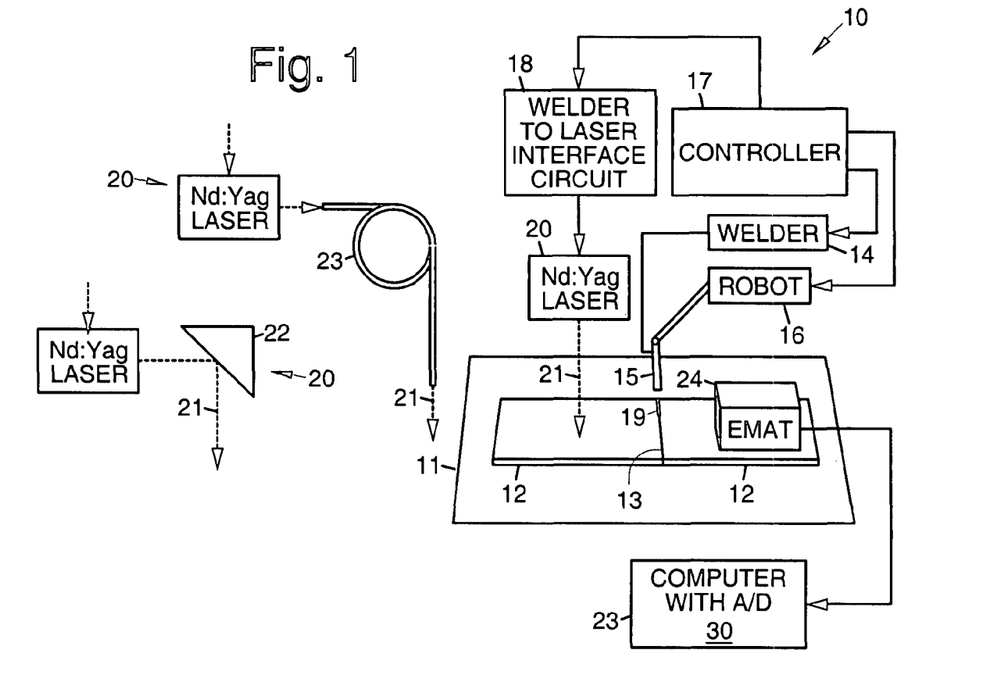
FIG. 1 illustrates an exemplary embodiment of an ultrasound system for measuring weld penetration depth.

Referring to the drawing figures, FIG. 1 illustrates an exemplary embodiment of an ultrasound system 10 for measuring weld penetration depth. Components of the ultrasound system 10 that perform the weld penetration depth measurement are preferably designed for use at high temperatures and in harsh environments, so that they can operate in a real-time, on-line welding environment.

The exemplary ultrasound system 10 comprises an ultrasound source 20 is used to measure the weld penetration depth of a weld 19 (weld bead 19 or weld seam 19) made between two pieces of metal 12 (specimens 12). FIG. 1 shows two pieces of metal 12 that are to be welded together at a butt joint 13 using a robotic welding system. The two pieces of metal 12 are disposed on a welding table 11. The robotic welding system comprises a welding torch 15 that is attached to a robot 16. The welding torch 15 is coupled to a welder 14. The welding torch 15 and robot 16 are controlled by a controller 17. The controller 17 also outputs control signals to an interface circuit 18.

The robot 16 may be a model P-50 process robot manufactured by General Electric, for example. The controller 17 may be a model Al 32v robot controller manufactured by Automatix, for example. The welder 14 may be a Pulstar 450 welder manufactured by Millar, for example.

The exemplary ultrasound system 10 comprises an ultrasound source 20 that is coupled to the interface circuit 18 and which is turned on and off under control of the controller 17. The ultrasound source 20 is disposed on one side of the butt joint 13 and weld seam 19, and such that laser pulses 21 output thereby are caused to strike one of the piece of metal 12 substantially normal to its surface. An exemplary ultrasound source 20 may be a pulsed Nd:Yag laser 20 that outputs laser pulses 21 at 1064 nm, for example. An exemplary ultrasound source 20 may be a Surelite II Nd:Yag laser manufactured by Continum. An exemplary interface circuit 18 may be a Microchip PIC16F84 micro controller.

In another embodiment, the ultrasound source 20 may include a fiber optic link that routes the laser pulses 21 to strike the piece of metal 12. In yet another embodiment, the ultrasound source 20 may include a reflective mirror 22 that reflects the laser beam 21 onto the piece of metal 12. In yet another embodiment, the ultrasound source 20 may comprises a fiber bundle or multiple sets of fibers that route the laser pulses 21 to impinge upon the piece of metal 12.

The ultrasound source 20 simultaneously generates longitudinal and shear waves when the laser pulses 21 strike the surface of the piece of metal 12. This is an important aspect of the ultrasound system 10 and will be discussed in more detail below.

An ultrasonic sensor 24 that is capable of receiving and detecting shear and/or longitudinal waves is disposed on an opposite side of the weld seam 19 from the ultrasound source 20. An exemplary ultrasonic sensor 24 for use in an off-line system 10 may be a piezo-electric transducer 24, for example. An exemplary ultrasonic sensor 24 for use in a real-time system 10 may be an electro-magnetic acoustic transducer (EMAT) 24, for example, and which may be based upon an EMAT developed by the US Navy. An exemplary EMAT 24 comprises a permanent magnet that generates a static magnetic field and an oriented pick-up coil. When ultrasound transmitted through the specimen 12 interacts with the static magnetic field, eddy currents are induced in the coil, which corresponds to the received ultrasound signal.

A signal processor 23 or computer 23 that includes an analog to digital converter, such as a model 6012 PCI A/D made by Gage, for example, is coupled to the ultrasonic sensor 24 and processes signals output by the ultrasonic sensor 24. The signal processor 23 implements an algorithm 30 (or method 30) that computes the weld penetration depth from the signals output by the ultrasonic sensor 20, and which will be described in more detail below.

There are two key discoveries that enable the ultrasound weld penetration depth measurement system 10. The first discovery is that if both longitudinal and shear waves are generated at the same time on one (top) surface of a welded specimen 12, a Rayleigh (surface) wave (referred to as an RG wave) is generated on the opposite (bottom) surface due to interaction between the longitudinal and shear waves. The second discovery relates to the path the Rayleigh wave takes when generated on one side of the weld seam 19 and received by the ultrasonic sensor 24 on the other side of the weld seam 19.

The ultrasound system 10 implements an ultrasonic Rayleigh wave time of flight (TOF) measurement technique in order to measure weld penetration depth. Reduced-to-practice embodiments of the system 10 that utilize various Rayleigh wave TOF techniques for measuring weld penetration depth have proven to be highly accurate, precise, and repeatable. The Rayleigh wave TOF techniques for measuring weld penetration depth have been demonstrated to work both off-line after welding and in real-time during welding. The systems may utilize Rayleigh-generated-longitudinal-shear (RGLS), Rayleigh-generated-shear-longitudinal (RGSL), Rayleigh-generated-longitudinal-longitudinal (RGLL), and Rayleigh-generated-shear-shear (RGSS) TOF techniques, which refers to the types of waves that propagate through the pieces of metal 12 to the ultrasonic sensor 24. The type of ultrasonic sensor 24 that is used depends upon which type of wave ultimately reaches the sensor 24.

For non-contact ultrasound generation, a pulsed laser 20 and an electro-magnetic acoustic transducer (EMAT) 24 may be used as the ultrasound source 20 and ultrasonic sensor 24. Pulsed lasers 20 with nanosecond rise-times including Q-switched Neodymium doped Yttrium Aluminum Garnet (Nd:Yag) lasers 20 and transversely excited atmosphere (TEA) CO2 lasers 20 may be used to generate ultrasound. Using low power densities, thermoelastic generation can be achieved by rapid cycling of heat at an ultrasound generation point on a surface of a specimen 12. Thermal strain at the ultrasound generation point causes a shearing motion within the specimen 12. At higher power densities, ablation occurs and the surface recoils. Both of these techniques create ultrasonic waves within a specimen 12. In general, the ablative laser generation methods create stronger ultrasound.

Figure 2:
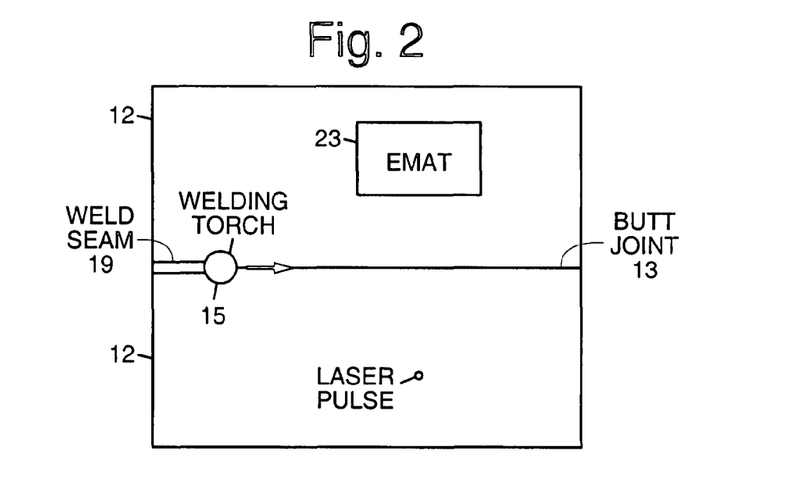
FIG. 2 is a top view of a portion of the exemplary ultrasound system.

FIG. 2 is a top view of a portion of the exemplary ultrasound system 10. FIG. 2 shows that the laser pulses 21 output by the ultrasound source 20 impinge upon one side of the weld seam 19, while the ultrasonic sensor 24 is located on the other side of the weld seam 19. The laser pulses 21 output by the ultrasound source 20 and the ultrasonic sensor 24 are disposed along a line that is substantially perpendicular to the weld seam 19. The ultrasound source 20 and the ultrasonic sensor 24 are also disposed downstream of the welding torch 15, so that the weld has time to solidify prior to weld penetration depth measurement.

Figure 3:
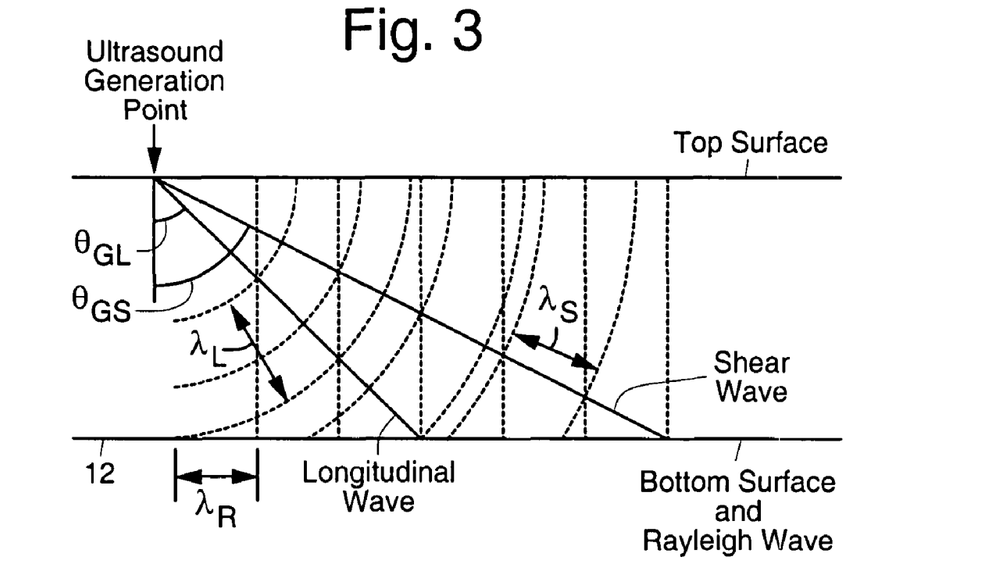
FIG. 3 illustrates determination of $\lambda_L$ and $\lambda_S$ for Rayleigh wave generation on a bottom surface of a specimen.
Figure 4:
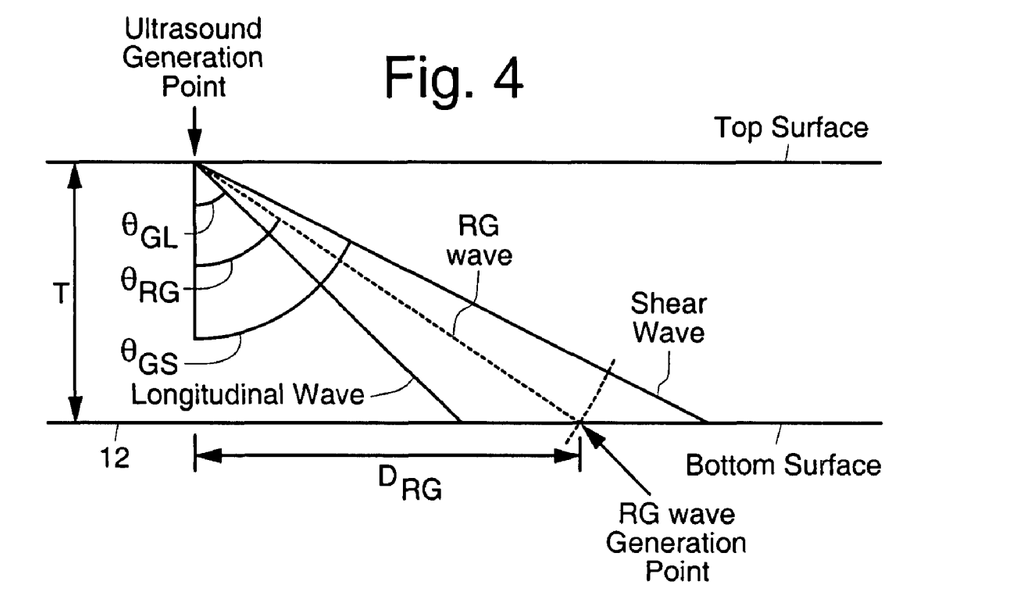
FIG. 4 illustrates generation of Rayleigh (RG) waves.

Referring to FIG. 3, it illustrates determination of $\lambda_L$ and $\lambda_S$ for Rayleigh wave generation on a bottom surface of a specimen 12. FIG. 4 illustrates generation of Rayleigh (RG) waves.

By way of introduction, ultrasonic bulk waves and ultrasonic surface waves are produced in the specimen 12. In isotropic solids, two types of bulk waves can be produced: shear (transverse) and longitudinal (compression). The two waves travel at different speeds through a given material: shear speed $C_s$ and longitudinal speed $C_L$ given by the equations immediately below. These speeds depend on the equations immediately below, where $\lambda$ and $\mu$ are Lame constants and $\rho$ is the density. In steel, longitudinal waves travel at 5960 m/s whereas shear waves travel at 3240 m/s.

$$C_S = \sqrt{\frac{\mu}{\rho}}$$

$$C_L = \sqrt{\frac{\lambda + \mu}{\rho}}$$

When either a shear or longitudinal wave reflects from a flat boundary, shear and longitudinal waves are created. The equations immediately below may be used to calculate amplitudes and reflection angles of the two reflected waves.

For incident longitudinal waves:

$$\theta_L = \theta_I$$

$$\sin\theta_S = \kappa^{-1}\sin\theta_I$$

$$\frac{A_L}{A_I} = \frac{\sin 2\theta_I \sin 2\theta_S - \kappa^2 \cos^2 2\theta_S}{\sin 2\theta_I \sin 2\theta_S + \kappa^2 \cos^2 2\theta_S}$$

$$\frac{A_S}{A_I} = \frac{2\kappa \sin 2\theta_I \sin 2\theta_T}{\sin 2\theta_I \sin 2\theta_S + \kappa^2 \cos^2 2\theta_S}$$

For incident shear waves:

$$\theta_S = \theta_I$$

$$\sin\theta_L = \kappa \sin\theta_I$$

$$\frac{A_S}{A_I} = \frac{\sin 2\theta_I \sin 2\theta_L - \kappa^2 \cos^2 2\theta_I}{\sin 2\theta_I \sin 2\theta_L + \kappa^2 \cos^2 2\theta_I}$$

$$\frac{A_L}{A_I} = \frac{\kappa \sin 4\theta_I}{\sin 2\theta_I \sin 2\theta_L + \kappa^2 \cos^2 2\theta_I}$$

where $$\kappa = \frac{C_L}{C_S}$$

$\theta_I$: Angle of incidence of incident wave in relation to boundary normal, $\theta_L$: Angle of reflected longitudinal wave, $\theta_S$: Angle of reflected shear wave, $A_I$: Amplitude of incident wave, $A_L$: Amplitude of reflected longitudinal wave, and $A_S$: Amplitude of reflected shear wave.

Rayleigh waves are the primary surface waves. Rayleigh waves displace material in two different directions: a displacement normal to the surface and a displacement parallel to the propagation direction shifted 90° in relation to the normal displacement. The Rayleigh wave speed can be calculated with the equation immediately below by solving for C. The Rayleigh wave speed, $C_R$, is the real root C less than $C_S$.

$$\left(2 - \frac{C^2}{C_S^2}\right) - 4\left(1 - \frac{C^2}{C_L^2}\right)^{\frac{1}{2}}\left(1 - \frac{C^2}{C_S^2}\right)^{\frac{1}{2}} = 0$$

A vertical transverse wave, shear vertical (SV), can create a non-Rayleigh surface wave. If a SV wave is incident on a surface and the calculated reflection angle of the reflected longitudinal wave is complex, a non-Rayleigh surface wave will be created. The speed of this surface wave, $C_{sw}$, is dependent on the speed of the transverse wave as shown in the equation:

$$C_{SW} = \frac{C_S}{\sin\theta_L}$$

There are a number of distinct ways laser generation of ultrasound can occur, including thermoelastic and ablative. The mode of generation is selected by varying power density, the irradiated power per surface area.

Thermoelastic ultrasound generation involves focusing a pulsing laser on a surface of a specimen 12 with low power densities expands and contracts a small cylinder of the specimen 12 by thermoelastic expansion and contraction. Normal forces arising from thermoelastic expansion and contraction can be ignored since the height of the heated cylinder is very small compared to the diameter of the cylinder in metals. Along any vector on the surface that originates from the middle of the cylinder, forces generated from the expansion of the surface will appear as two forces: both originating from the middle of the cylinder, with equal magnitude, and with opposite directions along the vector.

A directivity pattern is the variation of the generated wave amplitude with respect to the angle measured from the surface normal pointing into the specimen 12. The directivity pattern created from a force dipole acting in the surface plane is given by the equations immediately below.

$$u_L \propto \frac{\sin\theta \sin 2\theta \sqrt{\kappa^2 - \sin^2\theta}}{(\kappa^2 - 2\sin^2\theta)^2 + 4\sin^2\theta\sqrt{1 - \sin^2\theta}\sqrt{\kappa^2 - \sin^2\theta}}$$

$$u_S \propto \frac{\kappa \sin 4\theta}{\kappa(1 - 2\sin^2\theta)^2 + 4\sin^2\theta\sqrt{1 - \sin^2\theta}\sqrt{1 - \kappa^2\sin^2\theta}}$$

where:

$\theta$: Angle measured from the surface normal pointing into the specimen 12, $u_L$: Directivity of longitudinal waves, and $u_S$: Directivity of shear waves.

The frequency of the generated wave depends on the time it takes to heat and cool the material. Pulsed lasers with nanosecond rise-times including Q-switched Nd:Yag lasers and TEA CO2 lasers can heat the material fast enough to generate ultrasonic waves.

The strongest ultrasound by thermoelastic generation occurs when differences between the heated and unheated temperatures of the specimen 12 is large. With elevated temperatures within a welded specimen 12, power density has to be increased to get a large temperature variation. At some threshold, the power density will be strong enough to ablate the specimen 12. When this point is reached, ablative ultrasound generation will dominate.

When the power density is increased enough to vaporize a small portion of the specimen 12, the surface recoils as mass leaves the specimen 12. This is known as ablative ultrasound generation. The force of the recoil can be modeled as an impulse force along the surface normal pointing within the specimen 12. Similar to the thermoelastic mode of generation, a pulsed laser with a fast enough rise time creates ultrasonic waves.

The directivity of the generated ultrasound by an impulse force is given by the equations immediately below:

$$u_L \propto \frac{2\kappa^2 \cos\theta (\kappa^2 - 2\sin^2\theta)}{(\kappa^2 - 2\sin^2\theta)^2 + 4\sin^2\theta\sqrt{1 - \sin^2\theta}\sqrt{\kappa^2 - \sin^2\theta}}$$

$$u_S \propto \frac{\sin 2\theta \sqrt{1 - \kappa^2 \sin^2\theta}}{\kappa(1 - 2\sin^2\theta)^2 + 4\sin^2\theta\sqrt{1 - \sin^2\theta}\sqrt{1 - \kappa^2\sin^2\theta}}.$$

Typically, stronger waves are created using the ablative mode of ultrasound generation than thermoelastic, especially in gas metal arc welding because of elevated specimen temperatures.

If a longitudinal wave is generated on the surface of a specimen 12, there is one propagation angle, $\theta_{GL}$, away from the generation point where the component of the longitudinal wavelength parallel to the surface is equal to the Rayleigh wavelength, as is shown in FIG. 3. Similarly, if a shear wave is generated on the surface of a specimen, there is one propagation angle, $\theta_{GS}$, away from the generation point where the component of the shear wavelength parallel to the surface is equal to the Rayleigh wavelength. The angles $\theta_{GL}$ and $\theta_{GS}$ can be determined by Equations 1 and 2 respectively.

$$\theta_{GL} = a\sin\left(\frac{\lambda_R}{\lambda_L}\right) = a\sin\left(\frac{\frac{C_R}{f}}{\frac{C_L}{f}}\right) = a\sin\left(\frac{C_R}{C_L}\right) \quad \text{Eq. 1}$$

$$\theta_{GS} = a\sin\left(\frac{\lambda_R}{\lambda_S}\right) = a\sin\left(\frac{\frac{C_R}{f}}{\frac{C_S}{f}}\right) = a\sin\left(\frac{C_R}{C_S}\right) \quad \text{Eq. 2}$$

where:

$\lambda_R, \lambda_S, \lambda_L$: Rayleigh shear and longitudinal wavelengths, $C_R, C_S, C_L$: Rayleigh shear and longitudinal wave speeds, and $f$: frequency of waves.

When both shear and longitudinal waves are generated at the same time on the surface and propagate along angles $\theta_{GL}$ and $\theta_{GS}$ respectively, an RG wave is generated between points where the shear wave and longitudinal wave strike the opposite surface, as shown in FIG. 3. Horizontal distance between ultrasound generation point and RG wave generation point, $D_{RG}$, can be calculated using Eq. 3. The time between ultrasound generation time and RG wave generation time, $t_{RG}$, can be calculated using Eq. 4. Laser ultrasound generated by the laser ultrasound source 20 generates shear and longitudinal waves at the same time and at the required angles.

$$D_{RG} = T \cdot \tan(\theta_{RG}) \qquad \text{Eq. 3}$$

$$t_{RG} = \frac{T}{C_s \cos(\theta_{RG})} \qquad \text{Eq. 4}$$

where:

$\theta_{RG}$: angle between $\theta_{GL}$ and $\theta_{GS}$

T: thickness of specimen 12 or distance between opposing surfaces of the specimen 12.

Figure 5:
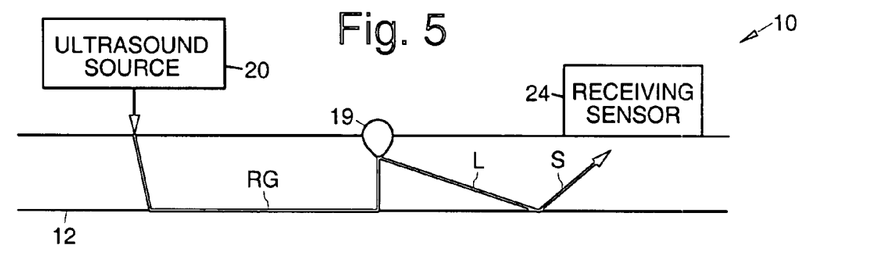
FIG. 5 illustrates placement of the ultrasound source and sensor with respect to a weld seam, the path of ultrasound energy in a welded specimen, and conversion of an RG wave into a RGLS mode converted wave.

FIG. 5 illustrates placement of the ultrasound source 20 and sensor 24 with respect to the weld seam, 19 the path of ultrasound energy in a welded specimen 12, and conversion of an RG wave into a RGLS mode converted wave. The path the RG wave takes when generated on one side of a weld seam 19 and received by the ultrasonic sensor 24 on the other side of the weld seam 19 enables the system 10 to measure weld penetration depth. Shear and longitudinal waves are generated on the top surface of the specimen 12. Once the RG wave is generated on the bottom surface of the specimen 12, the RG wave travels towards the weld seam 19. It then travels up from the bottom surface of the specimen 12 to the bottom of the weld bead 19 within the weld seam.

Figure 6:
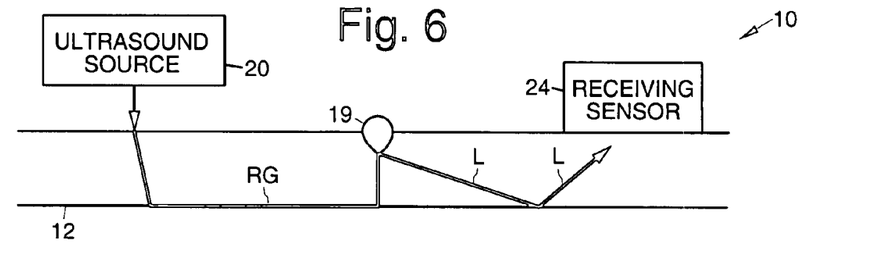
FIG. 6 illustrates conversion of an RG wave into a RGLL mode converted wave.

When the RG wave reaches the bottom of the weld bead 19, part of the wave's energy is converted into a longitudinal wave that travels back to the bottom surface of the specimen 12. At the bottom surface, part of the longitudinal wave's energy is mode converted to a shear wave, which is incident on the top surface where it is picked up by the ultrasonic sensor 24. This wave is referred to as an RGLS mode converted wave and is shown in FIG. 5. The remaining portion of the longitudinal wave's energy remains a longitudinal wave and can be picked up by the ultrasonic sensor 24. This wave is referred to as an RGLL mode converted wave and is shown in FIG. 6.

Figure 7:
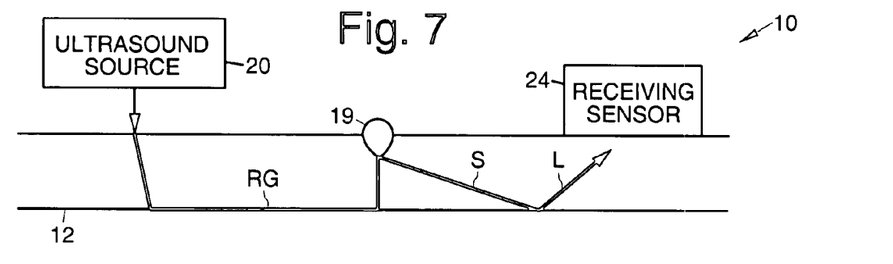
FIG. 7 illustrates conversion of an RG wave into a RGSL mode converted wave.
Figure 8:
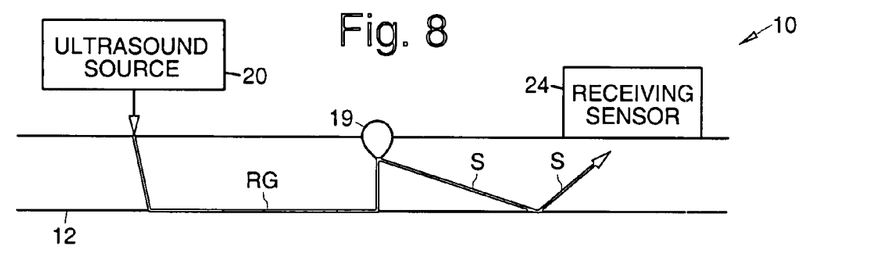
FIG. 8 illustrates conversion of an RG wave into a RGSS mode converted wave.

When the RG wave reaches the bottom of the weld bead, 19 part of the wave's energy is also converted into a shear wave that travels back to the bottom surface of the specimen 12. At the bottom surface, part of the shear wave's energy is mode converted into a longitudinal wave, which is incident on the top surface of the specimen 12, where it is picked up by the ultrasonic sensor 24. This wave is referred to as an RGSL mode converted wave and is shown in FIG. 7. Part of the shear wave's energy remains a shear wave and can be picked up by the ultrasonic sensor 24. This wave is referred to as an RGSS mode converted wave as shown in FIG. 8.

Since all of these waves travel from the bottom surface of the specimen 12 to the bottom of the weld bead 19, the propagation time or time of flight (TOF) of the waves depends on the weld penetration depth. Therefore, the weld penetration depth can be calculated by measuring the time of flight for any of the following mode converted waves: RGLS, RGLL, RGSL, and RGSS. Theoretical TOF for RGLS, RGLL, RGSL, and RGSS mode converted waves are given in Equations 5-8, respectively.

$$TOF_{RGLS} = \qquad \text{Eq. 5}$$
$$t_{RG} + \frac{(D_{GW} + T - PD - D_{RG})}{C_R} + \frac{T - PD}{C_L \cos(\theta_{L1})} + \frac{T}{C_S \cos(\theta_{S1})}$$

-continued $$RGLL_{TOF} = \qquad \text{Eq. 6}$$
$$t_{RG} + \frac{(D_{GW} + T - PD - D_{RG})}{C_R} + \frac{\sqrt{(2 \cdot T - PD)^2 + D_{WR}^2}}{C_L}$$

$$RGSL_{TOF} = \qquad \text{Eq. 7}$$
$$t_{RG} + \frac{(D_{GW} + T - PD - D_{RG})}{C_R} + \frac{T}{C_L \cos(\theta_{L1})} + \frac{T - PD}{C_S \cos(\theta_{S1})}$$

$$RGSS_{TOF} = \qquad \text{Eq. 8}$$
$$t_{RG} + \frac{(D_{GW} + T - PD - D_{RG})}{C_R} + \frac{\sqrt{(2 \cdot T - PD)^2 + D_{WR}^2}}{C_S}$$

where:

$C_R, C_S, C_L$: Rayleigh, shear, and longitudinal wave speeds, $t_{RG}$: Time for RG wave generation, $D_{RG}$: Horizontal distance between ultrasound generation point and RG wave generation point, $D_{GW}$: Distance between ultrasound generation point and weld seam, $D_{WR}$: Distance between the weld seam and the ultrasound sensor, T: Sample thickness or distance between opposite surfaces of the specimen, PD: Penetration depth of weld, $\theta_{S1}$: Reflection angle of shear wave from bottom surface of the specimen, and $\theta_{L1}$: Reflection angle of longitudinal wave from bottom surface of the specimen.

Equations 9 and 10 must be solved iteratively to find $\theta_{S1}$ and $\theta_{L1}$ for the RGSL mode converted wave.

$$\frac{\sin(\theta_{S1})}{C_S} = \frac{\sin(\theta_{L1})}{C_L} \qquad \text{Eq. 9}$$

$$D_{WR} = T \cdot \tan(\theta_{S1}) + (T - PD)\tan(\theta_{L1}) \qquad \text{Eq. 10}$$

$$D_{WR} = (T - PD) \cdot \tan(\theta_{S1}) + T \cdot \tan(\theta_{L1}). \qquad \text{Eq. 11}$$

Equations 9 and 10 are solved iteratively to find $\theta_{S1}$ and $\theta_{L1}$ for the RGLS mode converted wave, and equations 9 and 11 are solved iteratively to find $\theta_{S1}$ and $\theta_{L1}$ for the RGSL mode converted wave.

The algorithm 30 in the signal processor 23 or computer 23 computes the weld penetration depth using the above equations. The appropriate equation is easily solved to yield the penetration depth, since all of the other parameters are known.

Experimental results for 5 pre-welded specimens 12 using RGSL and RGLL TOF weld penetration depth measurements are given below in Tables 1 and 2. These experimental results indicate the performance capabilities of the ultrasound weld penetration depth measurement systems 10/

TABLE 1

RGLL method weld penetration depth measurement results

| Specimen Number | Actual penetration depth | RGLL TOF penetration depth | Difference | Absolute % error |
|---|---|---|---|---|
| E1 | 2.50E−03 | 2.47E−03 | 3.20E−05 | 1.28 |
| E2 | 3.70E−03 | 3.67E−03 | 3.60E−05 | 0.97 |
| E3 | 4.26E−03 | 4.18E−03 | 7.50E−05 | 1.76 |
| E4 | 5.34E−03 | 5.30E−03 | 3.50E−05 | 0.66 |
| E5 | 2.95E−03 | 2.98E−03 | −3.90E−05 | 1.32 |

Average % error 1.20
Minimum % error 0.66
Maximum % error 1.76
Standard deviation of difference 4.13E−05

TABLE 2

RGSL method weld penetration depth measurement results

| Specimen Number | Actual penetration depth | RGSL TOF penetration depth | Difference | Absolute % error |
|---|---|---|---|---|
| E1 | 2.50E−03 | 2.50E−03 | 1.00E−05 | 0.04 |
| E2 | 3.70E−03 | 3.72E−03 | −1.90E−05 | 0.51 |
| E3 | 4.26E−03 | 4.23E−03 | 2.90E−05 | 0.68 |
| E4 | 5.34E−03 | 5.29E−03 | 4.50E−05 | 0.84 |
| E5 | 2.95E−03 | 2.97E−03 | −2.70E−05 | 0.92 |

Average % error 0.60
Minimum % error 0.04
Maximum % error 0.92
Standard deviation of difference 3.08E−05

Figure 9:
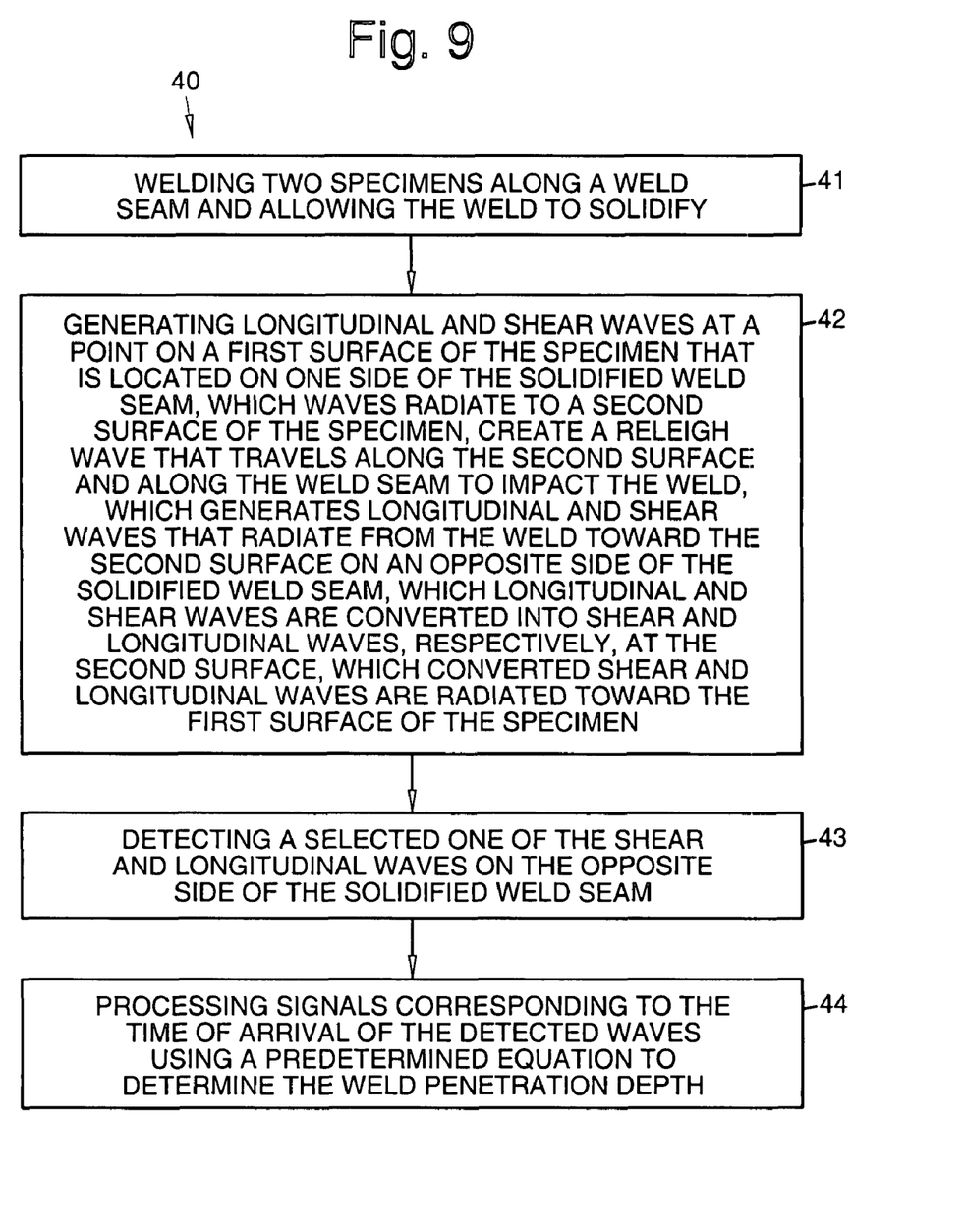
FIG. 9 is a flow diagram that illustrates an exemplary ultrasound weld penetration depth measuring method.

Referring to FIG. 9, it is a flow diagram that illustrates an exemplary ultrasound weld penetration depth measuring method 40. The exemplary ultrasound weld penetration depth measuring method 40 may be implemented as follows.

Two specimens 12 are welded 41 along a weld seam 19 and the weld is allowed to solidify. Longitudinal and shear ultrasound waves are generated 42 at a point on a first surface of the specimen 12 that is located on one side of the solidified weld seam 19, which waves radiate to a second (opposite) surface of the specimen 12, create a Rayleigh wave that travels along the second surface and along the weld seam 19 to impact the weld, which generates longitudinal and shear waves that radiate from the weld toward the second surface on an opposite side of the solidified weld seam 19, which longitudinal and shear waves are converted into shear and longitudinal waves, respectively, at the second surface, which converted shear and longitudinal waves are radiated toward the first surface of the specimen 12. A selected one of the shear and longitudinal waves is detected 43 on the opposite side of the solidified weld seam 19. Signals corresponding to the time of arrival of the detected waves are processed 44 using a predetermined equation to determine the weld penetration depth.

Thus, systems and methods that provide for both real-time and off-line measurement of weld penetration depth have been disclosed. It is to be understood that the above-described embodiments are merely illustrative of some of the many specific embodiments that represent applications of the principles discussed above. Clearly, numerous and other arrangements can be readily devised by those skilled in the art without departing from the scope of the invention.

What is claimed is:

1. An apparatus for measuring weld penetration depth, comprising:
    an ultrasound source for simultaneously generating longitudinal and shear waves on a first surface of a welded specimen on one side of a weld seam;
    an ultrasonic sensor disposed on an opposite side of the weld seam from the ultrasound source for detecting shear and/or longitudinal waves that are propagated from the one side of the weld seam to the opposite side; and
    a signal processor for processing time of flight signals corresponding to the time of arrival of the shear and/or longitudinal waves detected by the ultrasonic sensor using a predetermined equation to compute the weld penetration depth.

2. The apparatus recited in claim 1 wherein the longitudinal and shear waves generated on the first surface of the welded specimen radiate to a second surface of the specimen, create a Rayleigh wave that travels along the second surface and along the weld seam to impact the weld, which generates longitudinal and shear waves that radiate from the weld toward the second surface on an opposite side of the solidified weld seam, which longitudinal and shear waves are converted into shear and longitudinal waves, respectively, at the second surface, which converted shear and longitudinal waves are radiated toward the first surface of the specimen.

3. The apparatus recited in claim 1 wherein the ultrasound source comprises a pulsed Nd:Yag laser.

4. The apparatus recited in claim 3 wherein the selected one of the shear and longitudinal waves is detected using a piezo-electric transducer.

5. The apparatus recited in claim 1 wherein the ultrasonic sensor comprises an electro-magnetic acoustic transducer.

6. The apparatus recited in claim 1 wherein the ultrasonic sensor comprises a piezo-electric transducer.

7. An apparatus for measuring weld penetration depth, comprising:
    an ultrasound generator means for simultaneously generating longitudinal and shear waves on a first surface of a welded specimen on one side of a weld seam, which waves radiate to a second surface of the specimen, create a Rayleigh wave that travels along the second surface and along the weld seam to impact the weld, which generates longitudinal and shear waves that radiate from the weld toward the second surface on an opposite side of the solidified weld seam, which longitudinal and shear waves are converted into shear and longitudinal waves, respectively, at the second surface, which converted shear and longitudinal waves are radiated toward the first surface of the specimen;
    an ultrasonic sensor means for detecting shear and/or longitudinal waves disposed on an opposite side of the weld seam from the ultrasound source; and
    a signal processor means for processing signals corresponding to the time of arrival of the shear and/or longitudinal waves detected by the ultrasonic sensor using a predetermined equation to compute the weld penetration depth.

8. The apparatus recited in claim 7 wherein the ultrasound generator means comprises a pulsed Nd:Yag laser.

9. The apparatus recited in claim 7 wherein the ultrasonic sensor means comprises an electro-magnetic acoustic transducer.

10. The apparatus recited in claim 7 wherein the ultrasonic sensor means comprises a piezo-electric transducer.

11. A weld penetration depth measuring method comprising:

welding two specimens along a weld seam and allowing the weld to solidify; generating longitudinal and shear ultrasound waves at a point on a first surface of the welded specimen that is located on one side of the solidified weld seam, which waves radiate to a second surface of the specimen, create a Rayleigh wave that travels along the second surface and along the weld seam to impact the weld, which generates longitudinal and shear waves that radiate from the weld toward the second surface on an opposite side of the solidified weld seam, which longitudinal and shear waves are converted into shear and longitudinal waves, respectively, at the second surface, which converted shear and longitudinal waves are radiated toward the first surface of the specimen;

detecting a selected one of the shear and longitudinal waves on the opposite side of the solidified weld seam; and processing signals corresponding to the time of arrival of the detected waves using a predetermined equation to determine the weld penetration depth.

12. The method recited in claim 11 wherein the longitudinal and shear ultrasound waves are generated using a pulsed Nd:Yag laser.

13. The method recited in claim 12 wherein the selected one of the shear and longitudinal waves is detected using an electro-magnetic acoustic transducer.

* * * * *